United States Patent [19]  [11]  4,302,536
Longenecker  [45]  Nov. 24, 1981

[54] COLORIMETRIC IMMUNOASSAY PROCESS

[76] Inventor: Robert W. Longenecker, 6860 SW 113th St., Miami, Fla. 33156

[21] Appl. No.: 933,903

[22] Filed: Aug. 15, 1978

[51] Int. Cl.$^3$ .................... C12N 9/96; G01N 33/54; G01N 31/00
[52] U.S. Cl. ....................................... 435/7; 435/188; 23/230 B; 424/8; 424/12
[58] Field of Search .......... 195/99, 103.5 A, 103.5 R, 195/63; 23/230 B; 424/8, 12, 11; 435/7, 188; 260/112.5, 121

[56] References Cited

U.S. PATENT DOCUMENTS

| | | | |
|---|---|---|---|
| 2,194,131 | 3/1940 | Terry | 73/51 |
| 2,301,717 | 11/1942 | Terry | 424/90 |
| 3,069,330 | 12/1962 | Babson | 195/103.5 R |
| 3,144,484 | 8/1964 | Erlanger | 260/562 |
| 3,641,235 | 2/1972 | Weiss | 424/8 |
| 3,703,591 | 11/1972 | Bucolo et al. | 195/103.5 R |
| 3,853,987 | 12/1974 | Dreyer | 424/1 |
| 3,882,224 | 5/1975 | Forigione | 424/8 |
| 3,892,841 | 7/1975 | Barg | 424/12 |
| 3,949,065 | 4/1976 | Forgione | 424/8 |
| 3,966,897 | 6/1976 | Renn et al. | 424/1.5 |
| 3,985,867 | 10/1976 | Redshaw | 424/1.5 |
| 4,153,417 | 5/1979 | Hällgren | 424/8 |

FOREIGN PATENT DOCUMENTS 1180957  2/1970  United Kingdom .................... 424/8

OTHER PUBLICATIONS

Williams et al., Methods in Immunology and Immunochemistry, vol. 3, Academic Press, N.Y., (1971), pp. 294–321.
Otto et al., "Two Stage Method for Crosslinking Antibody Globulin to Ferritin by Glutaraldehyde".
"Comparison between the One-stage and Two-stage Methods", Chem. Absts., vol. 80, (1974), Abs. No. 144413p.
Shahrabachi et al., "Method for Staining Intracellular Antigens in Thin Sections with Ferritin-Labeled Antibody", Chem. Absts., vol. 75, (1971), Abs. No. 61339n.
De Grandi et al., "Ultrastructural Localization of Calcitonin in the Parafolliculture Cells of Pig Thyroid Gland with Cytochrome C Labeled Antibody Fragments", Chem. Absts., vol. 75, (1971), Abs. No. 61337k.
Eden et al., "Metalloimmunoassay", Nature, vol. 220, (1977), pp. 534–535.
Krachenbuhl et al., "Ultrastructural Localization of Intracellular Antigen Using Enzyme-labeled Antibody Fragments", Chem. Absts., vol. 75 (1971), Abs. No. 61338m.
Howe et al., "Application of Immunoferritin Techniques for the Detection of Viral and Cellular Antigens", Viral Immunodiagnosis, (1974), pp. 215–234.
Aurameas, "Coupling of Enzymes to Proteins with Glutaraldehyde", Immunochemistry, vol. 6, (1969), pp. 43–52.
Singer, "The Intracellular Localization of Parvovirus (H-1) Antigens Using Immunocytochrome-C", Viral Immunodiagnosis, (1974), pp. 101–123.
Wurzburg et al., "Quantitative Determination of Creative Kinase Isoenzyme Catalytic Concentrations in Serum Using Immunological Methods", J. Clin. Chem. Clin. Biochem., vol. 15, No. 3, (1977), pp. 131–137.
Kabat, Structural Concepts in Immunology and Immunochemistry, (1976), Holt, Rinehart and Winston, New York, pp. 74–78.
Hackh's Chemical Dictionary, 4th ed., McGraw-Hill Book Co., N.Y., (1969), pp. 157, 227.

Primary Examiner—Thomas G. Wiseman
Attorney, Agent, or Firm—Schuyler, Banner, Birch, McKie & Beckett

[57] ABSTRACT

Quantitative and qualitative measurement of antigenic materials present in blood serum or other biological fluids or cells is effected by an extremely precise and sensitive colorimetric immunoassay process. This process comprises adding to the sample to be tested a colorimetric immunoassay agent which comprises an adduct of (1) an antibody for the antigen to be tested and (2) a chromoprotein which is capable of chemically coupling to the antibody by covalent bonding and which chromoprotein imparts to the adduct a characteristic absorbance spectrum in the visible light wavelength range. After reacting this colorimetric immunoassay agent with the antigen to form a reagent-antigen complex, either in the complex-containing fraction or a fraction containing unreacted reagent can be analyzed using standard colorimetric equipment and procedures to provide a fast, simple and direct measurement of the antigen concentration in the sample.

13 Claims, No Drawings

COLORIMETRIC IMMUNOASSAY PROCESS

BACKGROUND OF THE INVENTION

1. Field of the Invention

This invention relates to immunoassay procedures for quantitative and qualitative determination of antigenic materials in body fluids or cells and, more particularly, to a simple, precise colorimetric procedure for this analysis.

2. Description of the Prior Art

The quantitation of the level of various analytes in human serum or other body fluids is an essential means of diagnosis in certain disease states, and is widely used in many clinical situations. It is important that the tests used for such determination possess the maximum possible sensitivity and freedom from interference.

For example, in the case of certain proteins, quantitation of the amount present must rely on special properties of such proteins. Two examples of this are fibrinogen, with the special property of forming solid masses (clots), and enzymes, whose special property is facilitation and catalysis of metabolic reactions in vivo. In each case, present techniques of measurement rely upon indirect observation of the protein's special property rather than by direct quantitation of the protein per se.

In the case of the fibrinogen, a material whose function is the initiation of the clotting process, such as thrombin, is added to the sample, and the reaction allowed to proceed to completion. The amount of fibrinogen present is measured by protein determinations on the sample before and after such reaction, the clottable protein (fibrinogen) being expressed as the difference in protein content before and after the clot is formed and removed from the solution.

Similarly, in the case of enzyme tests, the present means of performing quantitative determinations rely on indirect means in which the enzyme is introduced into a premixed system, and its catalytic effect on the system is followed and quantified. No direct measurement of the amount of enzyme is provided for or is possible. Thus, any change in the system used for the test, i.e., the "substrate," may alter the change which the enzyme being measured produces, and, therefore, the value of the resulting measurement. In addition, other materials present in the sample being tested other than the enzyme may also cause a change in the test system. These interfering effects may be indistinguishable from the effect of the enzyme, and the error thus is introduced into the determination.

It would be desirable to measure the amount of materials such as those outlined above present in the sample directly rather than by indirect means. Such a direct measurement, however, requires extreme sensitivity since the amount of such materials present is usually very small. In the case of enzyme testing, the fact is compensated for in the present indirect methods by allowing the catalytic action to continue for varying periods of time. These lengthy procedures, however, introduce another opportunity for variation in result due to the change in test conditions, such as temperature, as the test is run.

The required sensitivity may be found in immunological test procedures, which are capable of detecting the presence of materials in minute quantities when an antibody to the material to be assayed has been produced, purified, and is then used as a reagent for measurement of the material in question. Immunoassay procedures currently employ radioactive isotopes bound to an antibody by measurement of the isotope level remaining after reaction with an antigen. An enzyme bound to an antibody is also employed in a similar fashion by measurement of conventional substrate absorbance changes at ultraviolet wavelengths. The third common means of measurement is by following the change in turbidity when antibody is added to a solution of antigen. This method is probably the least precise of all. Most conventional immunological tests rely for their quantitation on the reaction of the test system in a series of dilutions, the results being reported as the highest dilution (smallest concentration) of the material being analyzed which is capable of producing a "positive" reaction with the reagent (antibody). This method of measurement is deficient where more precise quantitation is desired. Moreover, all the methods currently employed utilize equipment which is inconvenient or frequently unavailable in routine laboratories.

Thus, it would be a significant improvement in the performance of such tests if the sensitivity of the immunological determinations could be applied to measurement of substances such as those set forth above in such a way that precise results could be obtained by direct measurement with devices ordinarily available in the routine laboratory.

SUMMARY OF THE INVENTION

It is, therefore, an object of the present invention to provide a procedure for the measurement of antigenic material such as enzymes or other similar substances in biological fluids or cells which enables the rapid, direct measurement of the antigenic material and which can be interpreted using a standard laboratory colorimeter.

It is also an object of the present invention to provide a procedure for the measurement of antigenic materials in biological fluids or cells which possesses a precision and sensitivity not now possible in the presently employed methods.

In accordance with these and other objectives, the present invention relates to a method for the quantitative and qualitative determination of antigens occurring in biological fluids and cells which comprises the steps of providing samples containing a biological fluid or cell material to be tested for a particular antigenic material; adding to the sample a colorimetric immunoassay reagent which comprises an adduct of (1) an antibody for the antigenic material to be tested and (2) a chromoprotein which is capable of being chemically coupled to the antibody by covalent bonding and which chromoprotein imparts to the adduct a characteristic absorbance spectrum in the visible light wavelength range; reacting the colorimetric immunoassay reagent with said antigentic material to form a reagent-antigen complex; separating this reaction mixture into a reagent-antigen complex-containing fraction and an unreacted reagent-containing fraction; measuring the absorbance of a solution of one of these fractions; and comparing the absorbance values measured in the previous step with a standard sample of known adduct concentration.

DETAILED DESCRIPTION OF THE INVENTION

The colorimetric immunoassay procedure of the present invention employs a colorimetric reagent which is a chemically combined adduct of an antibody and a chromoprotein which renders the adduct measurable in solution by colorimetric means.

The antibody component of the reagent is selected or produced by means known in the art for reaction with a specific antigenic material to be tested. Generally, antibodies are produced by administering the material to be tested to a selected organism under conditions and following a dosage schedule which produces an optimal immunological response. The organism is usually but not always mammalian. The antibody produced by the organism is then recovered from the body fluid such as plamsa or serum by means which include precipitation, molecular seiving, and/or chromatography.

The chromoprotein component of the reagent employed in the process of the present invention can be any protein which has the requisite color-containing moiety, and which can be chemically crosslinked to the antibody. Among the chromoproteins suitable for the practice of the process of the present invention are ceruloplasmin, cytochrome c, ferritin, and transferrin.

Ceruloplasmin has an absorbance maximum at or near 610 nanometers, contains copper in its structure, and also possesses ferroxidase activity. Thus, quantitation of ceruloplasmin in solution by direct colorimetric measurement at or near the absorbance maximum of the compound may be confirmed by determination of ferroxidase activity present, or by measurement of the bound copper present in the ceruloplasmin.

Cytochrome c, in its reduced form, has absorbance maxima at or near 410, 520 and 550 nanometers, and also contains iron as a part of its structure. The quantitation in solution accomplished by direct colorimetric measurement of the reduced form at or near its absorbance maximum also may be confirmed by determination of the iron present. The absorbance spectrum of the oxidized form is also characteristic, with maxima at or near 410 and 529 nanometers, and may also be employed where appropriate.

Ferritin and transferrin also contain iron as part of their structure as well as a characteristic absorbance spectra, and may be employed in the same general manner.

Irrespective of which particular chromoprotein is employed, steps should be taken to ensure that it is utilized at essential homogeneity. This requires refinement of the ordinary available material by any of several means known to the art such as molecular seiving, recrystallization and/or chromatography in any form.

The antibody and chromoprotein components of the reagent of the present invention are chemically coupled to one another by the use of a poly-functional coupling agent. Coupling agents of this type are well known in the art and include carbodiimides, glutaraldehyde, metaxylene diisocyanate, and the like.

The cross-linking or conjugation process is known in the art. Briefly, the antibody, chromoprotein, and coupling agent are brought together under conditions which favor the coupling process, typically a buffer in the range of pH 6.0 to 8.0 and ionic strength of 0.05 to 0.15. The reactants are present in stoichiometric amounts as previously calculated and/or determined by titration, except that the chromoprotein to be coupled is present in excess, typically approximately twofold. The reaction is allowed to proceed at a temperature of 4° C. to 37° C. until the reaction is complete, typically about 4 to 18 hours. The mixture of chromoprotein-antibody adduct, unreacted chromoprotein, and unreacted coupling agent are then separated from each other by known means such as fractional precipitation, molecular seiving, and/or chromatography. The portions containing the antibody-chromoprotein complex are preserved by any of several applicable methods such as sterile filtration or lyophilization. The portions containing the excess unreacted chromoprotein can be reused, and the portions containing unreacted coupling agents are typically discarded. For a more detailed discussion on the methods for producing the chromoprotein-antibody conjugants employed in the present reaction, see Howe, et al, "Application of Immunoferritin Techniques For The Detection of Viral and Cellular Antigens," *Viral Immunodiagnosis,* p. 215–234 (1974); Avrameas, *Immunochemistry,* Vol. 6, p. 43 (1969).

The chromoprotein-antibody reagents employed in the process of the present invention are known but have only been employed in a different manner, namely in electron microscopy examinations of antigenic material in which the reagent is used in a manner analogous to a stain upon fixed material; see Singer, "The Intracellular Localization of Parvovirus (H-1) Antigens Using Immunocytochrome-c", *Viral Immunodiagnosis,* p. 101–123 (1974).

The reagent described above may be used for the detection and quantitation of numerous antigenic materials. Among the materials which can be determined in the process of the present invention are whole enzymes, enzyme fractions, proteins, protein fragments, blood group antigens, bacterial antibodies and the like. While by no means exhaustive, the following list of specific materials can be readily detected according to the method of the present invention: fibrinogen, gamma globulin, cholinesterase, isoenzymes of lactate dehydrogenase, and anti-streptolysin O.

The above-described reagent can be employed in a variety of configurations. For example, it can be used as a liquid solution or in solid form after being attached to a nonreactive support. In the preferred embodiment of the process of the present invention an excess of the reagent as described above is first combined with a solution containing the antigen to be quantitated and allowed to react for a period of time sufficient to allow attachment of the reagent to the antigen present. The reagent-antigen complex is then separated into a complex-containing fraction and a fraction containing unreacted reagent. This separation is accomplished by known means such as precipitation, chromatography, and the like. In the case of precipitation, which is the preferred method, the absorbance of the supernatant solution containing the unreacted reagent is read in a spectrophotometer at a wavelength appropriate to the absorbance spectrum of the chromoprotein moiety. The concentration of antigen in the samples assayed is, under these conditions, proportional to the amount of complex (reagent) removed by the reaction, and is thus inversely proportional to the absorbance of the remaining uncombined reagent in solution. The reference point for determination is a solution identically processed but lacking antigen in which the quantitation may be performed by reference to the test result with a sample or series of samples of known analyte content.

Alternatively, the reagent-antigen complex-containing fraction which has been isolated as described above can be quantitated. In this process the supernatant containing the unreacted reagent is removed, and the complex is resolubilized by known methods using appropriate salts, surfactants, solvents and the like. In this instance, the absorbance of the resulting solution is directly proportional to the level of antigen in the original solution.

When employing the reagent in the reactive support mode the reagent, affixed to an insoluble support, can be allowed to react with the material to be assayed in the manner described above. Following the initial reaction, the support containing the attached reacted and unreacted reagent is removed from contact with the sample and treated to solubilize only the reacted complex which is then quantitated colorimetrically as described above. Alternatively, only the unreacted reagent can be solubilized followed by the same quantitation as described above.

The following Examples are included for illustrious purposes only and are not intended to limit the scope of the invention.

EXAMPLE 1

In this example, the process of the present invention is employed to quanitatively measure fibrinogen in a plasma sample. The colorimetric immunoassay reagent comprises anti-fibrinogen produced in a rabbit, coupled to reduced cytochrome c with glutaraldehyde as a cross-linking agent. The resulting adduct has an absorbance maximum in the region of 550 nm.

One hundred microliters of plasma containing approximately 0.1 to 0.5 milligrams of fibrinogen are diluted with 1.9 ml of buffer containing appropriate salts to bring the ionic strength to 0.15. To this volume is added 1.0 ml of reagent containing 1.0 milligram equivalents of the reagent. A milligram equivalent is defined as the amount of reagent, previously determined, which bonds to 1 milligram of the fibrinogen. The absorbance of the resulting solution is read at 550 nm in a standard colorimeter, with air, distilled water or buffer as a reference blank. Typically, the absorbance in a one centimeter light path may be in the range of 0.50 to 0.80. The mixture then is reacted for one hour at 37° C. To the reaction mixture is added 2.0 ml of a solution of 20% glycine containing 1 mg/ml sodium ascorbate, in a buffer at pH 8.0. The resulting precipitate is separated by centrifugation at approximately 2000–5000 xg. The supernatant is decanted and its absorbance is read against a blank, similarly treated, but lacking fibrinogen. The reduction in absorbance of the solution when compared to the unreacted blank is proportional to the fibrinogen present in the original material by direct arithmetical calculation, or by comparison with a calibration curve prepared by performing the test upon a series of reference solutions of known fibrinogen content. Such a calibration plot is constructed with the $A_{550}$ on the ordinate and the concentration of the known solution as the abcissa. The concentration of the blank solution (zero fibrinogen content) in the above example thus corresponds to the maximum absorbance.

EXAMPLE 2

The procedures of Example 1 are repeated except that the reagent is prepared using an antibody to gamma globulin or a fragment thereof. Qualitative and quantitative detection of gamma globulin is thus effected in a rapid and precise manner.

EXAMPLE 3

The procedures of Example 1 are repeated except that the reagent is prepared using an antibody to the enzyme cholinesterase. Precise colorimetric assay is achieved.

EXAMPLE 4

This example demonstrates the determination of isoenzyme propositions within an enzyme. The reagent is formed from a previously prepared antibody to the enzyme lactate dehydrogenase, and specifically to that form of the enzyme which is characteristic of heart muscle, known as $LD_1$. This form is one of five possible combinations of the two monomers known to comprise the structure of the enzyme, the various different combinations each arising in a characteristic tissue.

The sample is diluted so that, in the subsequent test, the absorbance change in the measured supernatant is not reduced by more than approximately 65% when compared to the absorbance of the unreacted reagent at the same dilution. This is usually found to be at an enzyme level of about 500 IU (measurement according to the lactate substrate method at 37C). A second reagent, prepared with antibody to a combination of all five enzyme configurations may be employed as a second reference in the same manner.

The sample is combined with the reagent, in this case cytochrome c, in a proportion having previously been determined to permit optimum reaction. This will vary with different reagennt preparations, and is usually standardized by maintaining the sample volume and dilution constant and adjusting the concentration of the reagent in a constant volume. Typically, the sample is diluted with four volumes of buffer. An equal volume of reagent, appropriately diluted with buffer, is then added and the mixture allowed to incubate for thirty minutes at 37C. The buffer preferably contains a reducing agent to keep the reagent in its reduced form where greatest sensitivity lies. A blank tube is prepared in an identical manner, except that the sample is replaced with buffer. The absorbance is measured, at about 550 nm (in the case of the reagent employing cytochrome c as its chromogen) and falls in the range of 0.5 to 0.8 A against distilled water.

At the conclusion of incubation, a precipitating reagent is added for the antigen-antibody complex as may have been formed. Suitable precipitating agents include polyethylene glycol, inorganic salts such as ammonium salts, volatile solvents such as ethanol, and the like. The concentration of the precipitating agent is such that no more than a volume equal to the original sample dilution volume is required. The insolubilized complex is then removed by filtration or centrifuging, and the absorbance of the supernatant determined. In a normal sample this value may fall in the area of 0.3 to 0.5 A. In a sample of abnormal or elevated level, the value may fall in the area of 0.1 to 0.2 A. Samples producing a measured absorbance lower than 0.1 A should be repeated at a higher dilution.

Calibration of the test may be secured by reference to (1) the reduction of absorbance of the test compared to the blank reagent and thus in absolute "units" which are arbitrary, (2) a previously performed series of determinations on samples of known value, or (3) in conjunction with a parallel test with the reagent prepared with antibody to the "whole" enzyme, the result being in this case a proportion of the aborsbance change from the $LD_1$ compared to the change produced by measurement of all of the forms present. The latter is the preferred form.

EXAMPLE 5

This example demonstrates the determination of a blood-group specific substance on erythrocytes. The reagent is prepared in the manner of Example 1 except that the antibody is one specific to the desired blood group substance (Witebsky). Washed cells of an unknown group are combined with a standard quantity of the reagent for reaction. The cells are then removed and the absorbance of the supernatant is measured and quantitated as described in Example 1.

EXAMPLE 6

This example demonstrates the determination of anti-streptolysin O. The reagent is prepared in the manner of Example 1 except that streptolysin O is employed.

A presumptive, or screening test may be performed by first combining the sample with a previously determined amount of nonconjugated streptolysin O, which amount corresponds to an antibody level in the sample defined as normal. A known amount of the conjugated streptolysin O (reagent) is then added, and the absorbance of the unbound reagent determined following separation as previously described. An absorbance lower than that previously determined as normal by standardization against samples of known value indicates the presence of abnormal levels of antibody in the sample.

If reduction in the measured absorbance because of the presence of additional antibody is observed in the above test, quantitation may be obtained by addition of serial dilutions of the sample to a constant volume of the reagent. The anti-streptolysin level is then determined by comparison with unreacted reagent, or by reference to a calibration series, using samples of known antibody level.

While certain specific embodiments of the invention have been described with particularity herein, it should be recognized that various modifications thereof will appear to those skilled in the art. Therefore, the scope of the invention is to be limited solely by the scope of the claims appended hereto.

I claim:

1. A method for the qualitative and quantitative determination of antigenic materials in biological fluids and cells, said method comprising the steps of:
    (a) providing a sample containing a biological fluid or cell material to be tested for given antigenic material;
    (b) adding to said sample a colorimetric and immunoassay reagent, said reagent comprising an adduct of (i) an antibody for said antigenic material and (ii) a chromoprotein selected from the group consisting of ferritin, transferrin, cytochrome c, and ceruloplasmin, which chromoprotein is capable of being chemically coupled to said antibody by covalent bonding, said chromoprotein imparting to said adduct a characteristic absorbance spectrum in the visible light wavelength range;
    (c) reacting said colorimetric immunoassay reagent with said antigenic material to form a reagent-antigen complex;
    (d) separating the reaction mixture of step (c) into a reagent-antigen complex-containing fraction and an unreacted reagent-containing fraction;
    (e) measuring the absorbance of a solution of one of said fractions at the characteristic absorbance wavelength of said adduct; and
    (f) comparing the absorbance values measured in step (e) with an external standard sample of known adduct concentration.

2. The method of claim 1 additionally comprising the step of measuring one of said fractions for a property of said chromoprotein other than absorbance.

3. The method of claim 2 wherein said other property is a characteristic metal content.

4. The method of claim 2 wherein said other property is a characteristic enzymatic activity.

5. The method of claim 1 wherein said antigenic material is selected from the group consisting of enzymes, enzyme fractions, nonenzyme proteins and protein fractions, blood group antigens and bacterial antibodies.

6. The method of claim 1 wherein said antibody is coupled to said chromoprotein by a polyfunctional cross-linking agent.

7. The method of claim 6 wherein said cross linking agent is selected from the group consisting of carbodiimides, glutaraldehyde and metaxylene diisocyanate.

8. The method of claim 1 wherein said colorimetric immunoassay reagent is employed in solution form.

9. The method of claim 1 wherein said colorimetric immunoassay reagent is employed in solid form after being attached to a nonreactive support.

10. The method of claim 1 wherein the absorbance of said unreacted reagent-containing fraction is measured at the characteristic absorbance wavelength of said adduct.

11. The method of claim 10 wherein said reagent-antigen complex is separated from said unreacted reagent by precipitation of said complex.

12. The method of claim 1 wherein the absorbance of said reagent-antigen complex is measured at the characteristic absorbance wavelength of said adduct.

13. The method of claim 12 wherein said reagent-antigen complex is separated from said unreacted reagent by precipitation, and then the complex-containing precipitate is resolublized for absorbance measurement.

* * * * *